US009145378B2

(12) United States Patent
Muppa et al.

(10) Patent No.: US 9,145,378 B2
(45) Date of Patent: Sep. 29, 2015

(54) MANUFACTURE OF AN EPOXYETHYL ETHERS OR GLYCIDYL ETHERS

(75) Inventors: Prasad Muppa, Vondelingenplaat (NL); Ron Postma, Vondelingenplaat (NL); Caspar Schoolderman, Vondelingenplaat (NL); Sandra Rens, Vondelingenplaat (NL); Kostas Stoitsas, Vondelingenplaat (NL)

(73) Assignee: HEXION INC., Columbus, OH (US)

( * ) Notice: Subject to any disclaimer, the term of this patent is extended or adjusted under 35 U.S.C. 154(b) by 0 days.

(21) Appl. No.: 13/574,704

(22) PCT Filed: Jan. 26, 2011

(86) PCT No.: PCT/EP2011/000321
§ 371 (c)(1),
(2), (4) Date: Sep. 12, 2012

(87) PCT Pub. No.: WO2011/095293
PCT Pub. Date: Aug. 11, 2011

(65) Prior Publication Data
US 2012/0330041 A1 Dec. 27, 2012

(30) Foreign Application Priority Data
Feb. 2, 2010 (EP) .................................. 10001040

(51) Int. Cl.
*C07D 301/06* (2006.01)
*C07D 301/03* (2006.01)
*C07D 301/12* (2006.01)

(52) U.S. Cl.
CPC .................................. *C07D 301/12* (2013.01)

(58) Field of Classification Search
CPC ..................................................... C07D 301/12
USPC ......................................... 549/524, 531, 523
See application file for complete search history.

(56) References Cited

U.S. PATENT DOCUMENTS

| 4,021,454 | A | | 5/1977 | Wulff et al. |
| 4,038,291 | A | | 7/1977 | Gipson |
| 4,127,594 | A | | 11/1978 | Anderson et al. |
| 4,973,718 | A | | 11/1990 | Buchler |
| 5,153,161 | A | | 10/1992 | Kerschner et al. |
| 5,155,274 | A | | 10/1992 | Herrmann et al. |
| 5,274,147 | A | | 12/1993 | Kerschner et al. |
| 5,329,024 | A | | 7/1994 | Jureller et al. |
| 5,429,769 | A | | 7/1995 | Nicholson et al. |
| 5,516,738 | A | | 5/1996 | Jureller et al. |
| 5,532,389 | A | | 7/1996 | Trent et al. |
| 5,833,755 | A | | 11/1998 | Schlon et al. |
| 6,087,513 | A | * | 7/2000 | Liao et al. ..................... 549/524 |
| 6,500,968 | B2 | | 12/2002 | Zhou et al. |
| 6,673,950 | B1 | | 1/2004 | Teles et al. |
| 8,729,282 | B2 | | 5/2014 | Postma et al. |
| 2001/0025695 | A1 | | 10/2001 | Patt et al. |
| 2002/0010120 | A1 | | 1/2002 | Hage et al. |
| 2006/0041150 | A1 | | 2/2006 | Catinet et al. |
| 2010/0029848 | A1 | | 2/2010 | Forlin et al. |
| 2011/0137055 | A1 | | 6/2011 | Postma et al. |
| 2013/0006001 | A1 | | 1/2013 | Muppa et al. |

FOREIGN PATENT DOCUMENTS

| CN | 1900071 | 1/2007 |
| DE | 19923121 | 11/2000 |
| EP | 0458397 | 5/1991 |
| EP | 0458398 | 5/1991 |
| EP | 0618202 A | 10/1994 |
| EP | 1403219 | 3/2004 |
| EP | 1883730 | 2/2008 |
| EP | 2149569 | 2/2010 |
| EP | 2149570 | 2/2010 |
| EP | 2402087 | 1/2012 |
| JP | 2002145872 | 5/2002 |
| TW | 305831 | 6/1995 |
| TW | 200823183 | 6/2008 |
| WO | WO 2007/046960 | 4/2007 |

OTHER PUBLICATIONS

D.E. De Vos et al., Tetrahedron Letters, vol. 39, No. 20 (1998) 3221-3224.
Murphy et al., Organic Letters, American Chemical Society, vol. 6, No. 18 (2004) 3119-3122.
J.W. De Boer, "cis-Dihydroxylation and Epoxidation of Alkenes by Manganese Catalysts Selectivity, Reactivity and Mechanism", Feb. 22, 2008, Dissertation, University of Groningen, PrintPartners Ipskamp BV, Enschede, the Netherlands.
N.O. Brace et al., "Hydrophobic Compounds and Polymers from Long Chain Alkanamide-Formaldehyde Condensation Reactions", Journal of Organic Chemistry (1961) vol. 26, 5176-5180.
A. Grenz et al., "Synthesis and application of novel catalytically active polymers containing 1,4,7-triazacyclononanes", Chem. Commun. (2001) No. 18, 1726-1727 (Cambridge, England).
J.W. De Boer, "Mechanism of Cis-Dehydroxylation and Epoxidation of Alkenes by Highly H2O2 Efficient Dinuclear Manganese Catalysts," with Online Supporting Information, Inorganic Chemistry (2007), vol. 46, No. 16, pp. 6353-6372, American Chemical Society.
Z. Xi et al., "An Environmentally Benign Route for Epochlorohydrin From Allyl Chloride Epoxidation Catalyzed by Heteropolyphophatotungstate", Research on Chemical Intermediates (2007) vol. 33, No. 6, 523-534, VSP.

* cited by examiner

*Primary Examiner* — T. Victor Oh

(57) ABSTRACT

Processes are provided for the formation of an epoxyethyl ether or a glycidyl ether. In one embodiment, a process is provided for the manufacture of an epoxyethyl ether or glycidyl ether including reacting a vinyl ether or an allyl ether with an oxidant in the presence of a water-soluble manganese complex in an aqueous reaction medium, wherein the water-soluble manganese complex comprises an oxidation catalyst, characterized in that the water-soluble manganese complex is a mononuclear complex of the general formula (I): [LMnX$_3$]Y (I), or a binuclear complex of the general formula (II): [LMn($\mu$-X)$_3$MnL](Y)$_n$ (II), wherein Mn is a manganese; L or each L independently is a polydentate ligand, each X independently is a coordinating species and each $\mu$-X independently is a bridging coordinating species, Y is a non-coordinating counter ion, and wherein the epoxidation is carried out at a pH in the range of from 1.0 to 6.0. The invention also relates to epoxyethyl ethers.

19 Claims, No Drawings

MANUFACTURE OF AN EPOXYETHYL ETHERS OR GLYCIDYL ETHERS

RELATED APPLICATION DATA

This application claims the benefit of PCT Application PCT/EP2011/000321 with an International Filing Date of Jan. 26, 2011, published as WO 2011/095293, which PCT Application PCT/EP2011/000321 further claims priority to European Patent Application No. EP10001040.4 filed Feb. 2, 2010, the entire contents of both applications are hereby incorporated by reference.

FIELD OF INVENTION

The invention relates to a process for the manufacture of an epoxyethyl ethers or glycidyl ethers by catalytic oxidation of a vinyl ether or an allyl ether with an oxidant in the presence of a manganese complex.

BACKGROUND OF INVENTION

Epoxy ethers are an important starting material in the chemical industry. For instance, Heloxy® modifiers are epoxy functionalized alcohols, with originally one or more hydroxyl groups. These modifiers are offered for instance in the form of monofunctional glycidyl ethers, and polyfunctional glycidyl ethers. Modifiers help improve cured system flexibility, increase peel and impact strength, increase the level of filler loading, improve resin wetting action, and reduce viscosity and surface tension. In particular the polyfunctional glycidyl ethers are useful. Of similar relevance are the epoxidation products of vinyl ethers of alcohol, diols and polyols.

The glycidyl ethers may be prepared using epichlorohydrin and alcohols (diols and polyols). From an environmental perspective, finding an alternative route would be rather attractive. In the Journal of Molecular Catalysis A: Chemical 244 (2006) 173-178 by E. Kaczmarczyk et al "Epoxidation of 1,4-bis(allyloxy)butane by Hydrogen Peroxide Under Phase Transfer Catalysis" the preparation of the diglycidylether of 1,4-butanediol was investigated. Both a monoepoxide and a diepoxide were produced. Diallylether was epoxidized by Peng Wu et al, "A Novel Titanosilicate With MWW Structure Catalytic Properties In Selective Epoxidation Of Diallyl Ether With Hydrogen Peroxide" in Journal of Catalysis 228 (2004) 183-191.

In the Journal of Molecular Catalysis A: Chemical 235 (2005) 52-56 "Epoxidation of 1,4-Diallyloxybutane To 1-Allyloxy-4-Glycidyloxybutane By The Method Of Phase Transfer Catalysis" by E. Kaczmarczyk et al the epoxidation of 1,4-diallyloxybutane (DiAB) with 30 wt % hydrogen peroxide in the presence of phosphorotungstic acid (PTA) hydrate or phosphoric(V)-acid-sodium tungsten(VI) dihydrate system ($PO_4^{3-}/WO_4^{2-}$) as the catalysts and an (phosph) onium salt as a phase transfer catalyst was investigated. Again by E. Kaczmarczyk et al the epoxidation of 1,4-bis(allyloxy) butane was investigated in Journal of Molecular Catalysis A: Chemical 265 (2007) 148-152, "Selective Epoxidation Of 1,4-Bis(Allyloxy)Butane To 1-Allyloxy-Glycidoloxybutane In The Presence Of Ionic Liquids".

The inventors set out to find an alternative route to glycidyl ethers that does not rely on epichlorohydrin. Such an alternative route has been found. Moreover, this new route also opens the possibility of preparing epoxyethyl ethers which will find use in the same applications where the glycidyl ethers are used. The present invention provides an attractive route to such products.

DISCLOSURE OF THE INVENTION

Accordingly, the invention provides a process for the manufacture of an epoxyethyl ether or a glycidyl ether including reacting a vinyl ether or an allyl ether with an oxidant in the presence of a water-soluble manganese complex in an aqueous reaction medium, wherein the water-soluble manganese complex comprises an oxidation catalyst, characterized in that the water-soluble manganese complex is a mononuclear complex of the general formula (I): [$LMnX_3$]Y (I), or a binuclear complex of the general formula (II): [$LMn(\mu-X)_3MnL$]$(Y)_n$ (II), wherein Mn is a manganese; L or each L independently is a polydentate ligand, each X independently is a coordinating species and each μ-X independently is a bridging coordinating species, wherein Y is a non-coordinating counter ion, and wherein the reaction is performed at a pH in the range of from 1.0 to 6.0.

In one embodiment, the invention provides a process for the manufacture of an epoxyethyl ether or a glycidyl ether by catalytic oxidation of a vinyl or allyl ether using an oxidant, preferably hydrogen peroxide, and a manganese complex wherein the catalytic oxidation is performed in an aqueous reaction medium, comprising water with less than 10% by volume of co-solvents, wherein a water-soluble manganese complex may be used as oxidation catalyst, characterized in that the water-soluble manganese complex is a mononuclear species of the general formula (I): [$LMnX_3$]Y (I), or a binuclear species of the general formula (II): [$LMn(\mu-X)_3MnL$]$(Y)_n$ (II), wherein Mn is a manganese; L or each L independently is a polydentate ligand, each X independently is a coordinating species and each μ-X independently is a bridging coordinating species, wherein Y is a non-coordinating counter ion, and wherein the reaction is performed at a pH in the range of from 1.0 to 6.0. This process is particularly suitable for the preparation of diepoxides and polyepoxides.

The epoxidation products of the vinyl ethers are believed to be novel. Accordingly, this invention also relates to epoxyethyl ethers.

In one embodiment, the invention provides a process for the manufacture of an N-glycid compound, including reacting a N-allylamine with an oxidant in the presence of a water-soluble manganese complex in an aqueous reaction medium, wherein the water-soluble manganese complex comprises an oxidation catalyst, characterized in that the water-soluble manganese complex is a mononuclear complex of the general formula (I):

[$LMnX_3$]Y                                    (I)

or a binuclear complex of the general formula (II):

[$LMn(\mu-X)_3MnL$]$(Y)_n$                     (II)

wherein Mn is a manganese; L or each L independently is a polydentate ligand, each X independently is a coordinating species and each μ-X independently is a bridging coordinating species, wherein Y comprises a non-coordinating counter ion.

MODE(S) FOR CARRYING OUT THE INVENTION

As used in the current specification, the expressions epoxidation and oxidation refer to the same reaction; the conversion of the carbon-carbon double bond of the vinyl group or the allyl group into an oxirane ring. The invention is hereafter discussed in greater detail.

It is rather surprising that the current process can be used to prepare epoxyethyl ethers and glycidyl ethers, including diepoxides and polyepoxides with improved selectivity with having the reaction performed in an aqueous reaction medium. For example, the process has an improved selectivity towards epoxide products in comparison other components, such as diols, of 80% or greater. The epoxyethyl ethers and glycidyl ethers that may be made from a vinyl or an allyl ether include, for example, 1,2-epoxyethyl ether=ROCH—CH$_2$O and 2,3-epoxypropyl ether=ROCH$_2$CH—CH$_2$O, respectively.

In terms of water-soluble manganese complexes that may be used as oxidation catalyst, many suitable complexes are known. Note in this respect that what is described in this patent is actually the catalyst precursor. Indeed, in all open and patent literature typically a catalyst precursor is defined, as the active species during the system may be different and in fact even changing during the reaction that it catalyses. For convenience sake, and as this is common in the literature, we refer to the complex as if it is the catalyst.

In one embodiment, the catalyst comprises a manganese atom or a number of manganese atoms coordinated with a ligand or ligands. The manganese atom(s) may be in a II, III or IV oxidation state and be activated during the reaction. Of particular interest are binuclear manganese complexes. Suitable manganese complexes therefore include mononuclear species of the general formula (I):

[LMnX$_3$]Y   (I),

and binuclear species of the general formula (II):

[LMn(μ-X)$_3$MnL](Y)$_n$   (II),

wherein Mn is manganese. L or each L independently is a polydentate ligand, preferably a cyclic or acyclic compound containing 3 nitrogen atoms. Each X is independently a coordinating species and each μ-X is independently a bridging coordinating species, selected from the group consisting of: RO$^-$, Cl$^-$, Br$^-$, I$^-$, F$^-$, NCS$^-$, N$_3^-$, I$_3^-$, NH$_3$, NR$_3$, RCOO$^-$, RSO$_3^-$, RSO$_4^-$, OH$^-$, O$^{2-}$, O$_2^{2-}$, HOO$^-$, H$_2$O, SH$^-$, CN$^-$, OCN$^-$, and S$_4^{2-}$ and combinations thereof, wherein R is a C$_1$-C$_{20}$ radical selected from the group consisting of alkyl, cycloalkyl, aryl, benzyl and combinations thereof. Y is a non-coordinating counter ion. The non-coordinating counter ion Y may provide for the charge neutrality of the complex and the value of n depends upon the charge of the cationic complex and anionic counter ion Y, for example, n may be 1 or 2. Counter ion Y may for instance be an anion selected from the group consisting of RO$^-$, Cl$^-$, Br$^-$, I$^-$, F$^-$, SO$_4^{2-}$, RCOO$^-$, PF$_6^-$, tosylate, triflate (CF$_3$SO$_3^-$) and a combination thereof with R once again being a C$_1$ to C$_{20}$ radical selected from the group consisting of alkyl, cycloalkyl, aryl, benzyl and combination thereof The type of anion is not very critical, although some anions are more preferred than others. In one embodiment, an ion of CH$_3$COO$^-$ or PF$_6^-$ may be used as the non-coordinating counter ion.

Ligands which are suitable for the present invention are acyclic compounds containing at least 7 atoms in the backbone or cyclic compounds containing at least 9 atoms in the ring, each having the nitrogen atoms separated by at least two carbon atoms. A preferred class of ligands is that based on (substituted) triazacyclononane ("Tacn"). One suitable ligand is 1,4,7-trimethyl-1,4,7,-triazacyclononane (TmTacn) which is commercially available from for instance Aldrich. In this respect it is important to note that the water-solubility of the manganese catalyst is a function of all the aforementioned catalyst components. An advantage of the current invention in using a water soluble manganese complex is that the catalyst essentially does not migrate to the organic phase.

Binuclear manganese complexes are preferred, because of their greater activity and solubility in water. Preferred binuclear manganese complexes are those of the formula [Mn$^{IV}_2$(μ-O)$_3$L$_2$](Y)$_n$, (same as formula: [LMn(μ-O)$_3$MnL](Y)$_n$), wherein n is 2, and L and Y have the meaning identified above, preferably TmTacn as ligand, and CH$_3$COO$^-$ as counter ion.

According to the present invention, the manganese complex may be utilized directly or as adsorbed onto a solvent insoluble support surface. Illustrative but non-limiting examples of such substrates are structured aluminosilicates (e.g. Zeolite A, faujasite and sodalite), amorphous aluminosilicates, silica, alumina, charcoal, microporous polymeric resins (e.g. polystyrene beads formed through high internal phase emulsion technology) and clays (especially layered clays such as hectorite and hydrotalcite). Relative weight ratios of the manganese complex to the support may range anywhere from about 10:1 to about 1:10,000.

The manganese complex may be used in catalytically effective amounts. To achieve the high selectivity and turnover numbers of the current invention, the catalyst and oxidant are preferably combined for reaction with the vinyl ether or allyl ether at a molar ratio of catalyst to oxidant from 1:10 to 1:10,000,000, such as, from 1:100 to 1:1,000,000, for example, from 1:1000 to 1:100,000. The manganese complex may be used in a molar ratio of catalyst (Mn complex) versus hydrogen peroxide of from 1:10 to 1:10,000,000, such as from 1:100 to 1:1,000,000, for example of from 1:1000 to 1:100,000.

The reaction (catalytic oxidation) of the present invention is performed with an oxidant, preferably using hydrogen peroxide. Other oxidants may be used, i.e. as precursor to the hydrogen peroxide, but given the availability and to reduce environmental impact hydrogen peroxide is the preferred oxidant. Hydrogen peroxide has strong oxidizing properties, and may be used in an aqueous solution. The concentration of added hydrogen peroxide may vary, from 15% to 98% (propellant grade), with a preference for industrial grades varying from 20 to 80%, preferably from 30 to 70%. To ensure optimal oxidant efficiency, the oxidant is preferably added to the aqueous reaction medium at a rate about equal to the reaction rate of the catalytic oxidation. Other oxidants that may be used include organic peroxides, peracids, and combinations thereof.

The aqueous reaction medium may be a water phase containing the vinyl or allyl ether and/or their respective epoxidation products and less than 10% by volume, preferably only minor amounts, if any, of other organic compounds. Although not preferred, the reaction medium may contain minor amounts of co-solvents, for example, including acetone, methanol, and other water-soluble alcohols. Whilst excluding the presence of the reactants and their epoxidation products, the aqueous reaction medium therefore suitably comprises at least 90% by volume (v %) of water, preferably 95 v %, more preferably 99 v %, still more preferably 99.9 v % of water. In one embodiment, the aqueous reaction medium (again, excluding any reactants and/or their epoxidation products dissolved therein) is essentially a 100% water phase.

The aqueous reaction medium will contain a buffer system so as to stabilize the pH. For instance, it has been found that the aqueous reaction medium is suitably stabilized in a pH range of 1.0 to 6.0, whereas the preferred pH range is between 2.0 and 5.0. The suitable or preferred range may be achieved by several known organic acid-salt combinations, with the preferred combination being based on oxalic acid-oxalate salt, or acetate acid-acetate salt or oxalic acid-oxalate salt and acetic acid-acetate salt. When oxalic acid and sodium oxalate are used, the pH ratio may be varied from 2.0 to 6.0. The buffer may be used in a molar ratio to the catalyst of about 60:1, but the amounts may be varied broadly, e.g., ranging from 1:1 to 300:1.

The aqueous reaction medium may also contain a phase transfer agent and/or a surfactant. Known phase transfer agents that may be used in the process of the invention include quaternary alkyl ammonium salts. Known surfactants that may be used in the process of the invention include non ionic surfactants such as Triton X100™ available from Union Carbide.

It is believed to be beneficial that the aqueous reaction medium contains at least trace amounts of the starting vinyl or allyl ether. Although this is purely a hypothesis, it is believed that the presence of this starting material is beneficial to allow the catalyst to remain active. Whereas it is believed that without the presence of the vinyl ether or allyl ether (and/or due to the presence of the epoxidized product and/or oxidant without any starting material), the catalyst has a reduced activity. Additionally, it is believed that the presence of the epoxidized product and/or oxidant without any starting material present will also reduce the activity of the catalyst.

The reaction conditions for the catalytic oxidation may be quickly determined by a person skilled in the art. The epoxidation is carried out either under pressure or at atmospheric pressure. The reaction is believed to be exothermic, and cooling of the reaction medium may be required. The reaction is preferably carried out at temperatures anywhere from -5° C. to 40° C., preferably from 5° C. to 30° C.

The molar ratio a vinyl or allyl ether to oxidant affects the reaction and the products of the reaction. For example, if too much oxidant, such as hydrogen peroxide may be used, then the selectivity towards the desired epoxide reduces due to the production of undesirable side-products, such as diols, or involves a significant waste of the oxidant. If not enough oxidant is used, then the turnover number is suboptimal. This is therefore significantly different from bleaching conditions described in the prior art, where excessive amounts of an oxidant, such as hydrogen peroxide, are used. The molar ratio of a vinyl ether or allyl ether to an oxidant, such as hydrogen peroxide, may be in the range of from greater than 1:2. In one embodiment, the molar ratio of a vinyl ether or allyl ether to an oxidant, such as hydrogen peroxide, may be in the range of from greater than 1:1.2 to about 12:1, such as from about 1:1 to about 10:1 (or alternatively, from about 1:1.2 to about 2:1 or 2:1 to 12:1), for example, about 1:1. The ether is preferably used in excess over the oxidant.

The starting material used in the process of the current invention may be a vinyl or allyl ether based on a mono alcohol, a diol, a triol a tetraol or a polyol. Included therefore are ethers having more than one ether group within the molecule. It may be based on an aliphatic or aromatic alcohol. More preferably, divinyl ethers or diallyl ethers of diols are used, such as the divinyl ether of monoethylene glycol, or the divinylether of polyethylene glycol. Of similar relevance is the divinyl ether or diallyl ether of bisphenol-A or bisphenol-F or similar aromatic polyols. Also of interest are tri and tetra ethers, e.g., of pentaerythritol and of common sugars.

The starting material is preferably an ether of the general formulae:

O(CH=CH$_2$)$_2$; R(OCH=CH$_2$)$_2$;

O(CH$_2$CH=CH$_2$)$_2$; R(OCH$_2$CH=CH$_2$)$_2$,

R'OCH=CH$_2$; or

R'OCH$_2$CH=CH$_2$;

wherein R is a radical of one or more carbon atoms optionally containing one or more heteroatoms (such as oxygen, nitrogen or silicon) and R' is a bivalent radical of one or more carbon atoms optionally containing one or more heteroatoms, which may carry one or more vinyloxy or allyloxy substituent groups. Suitable examples include divinyl ether, diallyl ether, allyl n-butyl ether, n-butyl vinyl ether, vinyl allyl ether, ethyl vinyl ether, ethylene divinyl diether, 1,4-diglycidyl butylene diether, tetraallyl pentaerythritol tetraether, and combinations thereof.

Of particular interest as starting material are diols functionalized with allylic groups. These products may for instance be produced in a two step process. For instance, during a first step ethers may be prepared by dehydration of alcohols.

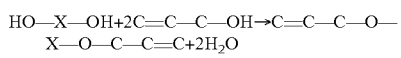

During a 2$^{nd}$ step epoxidation of the ethers may be carried out.

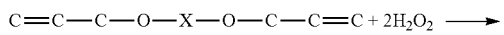
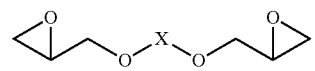

Of similar interest is the conversion of Bisphenol-A (BPA) or Bisphenol-F (BPF). As shown in the below reaction scheme, BPA (reaction scheme) can react with allyl alcohol in order to form the corresponding ethers. Epoxidation of the ethers will follow in order to form the corresponding epoxy resins.

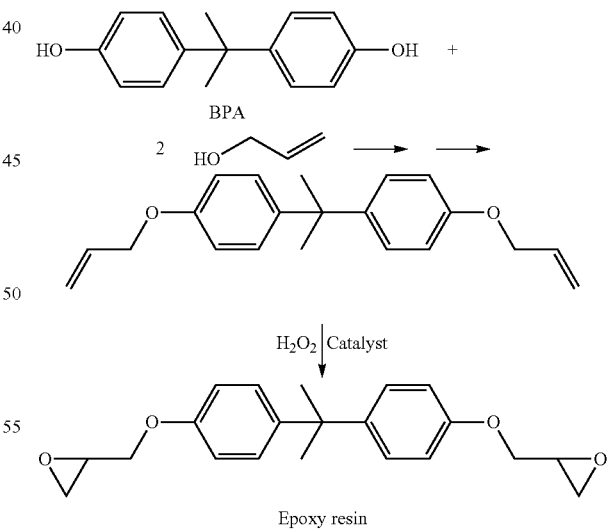

By a similar process, BPF can react with allyl alcohol in order to form the corresponding ethers. Vinyl ethers of BPA, for instance, may be produced through the reaction of vinyl chloride with an alkoxide of BPA, through the well known Williamson reaction, as described in "Advanced Organic Chemistry, Reactions, Mechanisms and Structure 5th edition M. Smith, J. March.

The epoxidation products of the vinyl ethers are believed to be novel. Accordingly, this invention also relates to such novel epoxyethyl ethers.

Thus, categories of vinyl and allyl ethers suitably used in the current invention include the following.

In one embodiment, the allyl eters and vinyl ethers are mono, bis (di), tris (tri), and poly-allyl ethers and mono, bis (di), tris (tri), and poly-vinyl ethers of aliphatic alcohols. The allyl ethers or vinyl ethers of the aliphatic alcohols may have primary, secondary or tertiary substitution. The allyl and vinyl ethers of aliphatic alcohols may have at least the following structures (Ia) and (Ib) where $R_1$, $R_2$, $R_3$ each independently comprises a hydrogen atom, a halogen atom, or a organic group having one or more carbon atoms, such as from 1 to 20 carbon atoms. Each of the organic groups may be a linear, a branched, or a cyclic organic group. Each of the organic groups may further be a substituted organic group with an allyl group including an allyl ether group, a vinyl group including a vinyl ether group, an alcohol group, a halogen atom, and combinations thereof. The organic group may further contain a non-carbon atom, including an oxygen atom (an ether group), a sulphur atom (a thiol group), a nitrogen atom (an amino group), and combinations thereof.

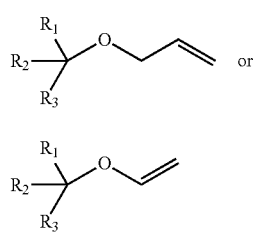

(Ia)

(Ib)

Examples of such compounds are, if possible, mono allyl, di allyl, and tri allyl ethers of trimethylolpropane, glycerine, 1,4-butanediol, cyclohexane dimethanol, 1,6-hexanediol, n-butanol, 1-decanol, 2-butoxyethanol, 2-ethylhexanol, 3-diethylamino-1,2-propanediol, dibromoneopentylglycol, butyl diglycol, neopentylglycol, dipropyleneglycol, pentaerythritol, trimethylolethane, 4,4'-(propane-2,2-diyl)dicyclohexanol, diglycerine, 2-butanol, abd combinations thereof. Allyl ethers of fatty alcohols having between 8 ($C_8$) to 15 ($C_{15}$) carbon atoms, including alcohols having carbon atoms of $C_8$-$C_{10}$, $C_{12}$-$C_{14}$, and $C_{13}$-$C_{15}$, may also be used in the process described herein.

Additional ethers compounds represented in this category include mono, bis (di), tris (tri) and poly-allyl ethers of polyglycols where n is 1 to 100, such as 7, prepared from the structure (II) of:

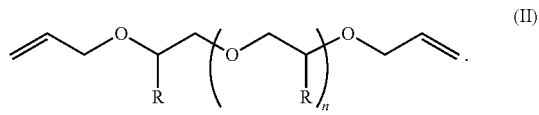

(II)

and poly-allyl ether of oils, which in one example, a poly-allyl ether of castor oil may form a castor oil polyglycidyl ether after reacting with the oxidant in the presence of the manganese complex.

Another class of substrate are poly-allyl or poly-vinyl ethers derived from carbohydrates, having a structure (III):

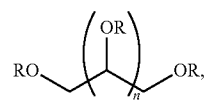

(III)

wherein each R is independently a hydrogen atom, a vinyl group, or an allyl group with at least one R being a vinyl group or an allyl group. The poly-allyl or poly-vinyl ethers of sugar alcohols further include derivatives thereof. Examples of such compounds include poly-allyl or poly-vinyl ethers of arabitol (5-carbon), xylitol (5-carbon), ribilol (5-carbon), erythritol (4-carbon), threitol (4-carbon), mannitol (6-carbon), dulcitol (6-carbon), and sorbitol (6-carbon), such as a tetra allyl ether of sorbitol.

Another category of suitable substrate are mono, bis (di), tris (tri), and poly-allyl and mono, bis (di), tris (tri), and poly-vinyl ethers of phenol derivatives and benzyl alcohols. This includes phenol derivatives of monophenol, bisphenol, trisphenol and polyphenol having at least a structure as described below, where R is either a carbon, hydrogen, halogen, nitrogen, sulphur, or oxygen atom, positioned on the ortho, meta or para position with respect to the allyloxy group:

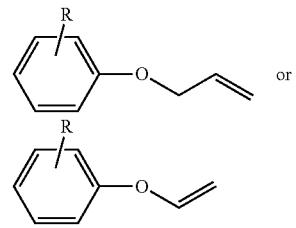

This includes, if possible, mono allyl, di allyl, and tri allyl ethers of phenol, 4-tert-butylphenol, 2,4-dibromophenol, 4-(1,1,3,3)-tetramethylbutylphenol, 4-(2-phenylisopropyl) phenol, nonylphenol, o-cresol, p-methoxyphenol, bisphenol A, tetra-bromo bisphenol A, bisphenol S, bisphenol F, bisphenol P, bisphenol M, p-tert butyl phenol, resorcine, styrenated phenol, tetraphenyloethane, trisphenol, benzyl alcohol, and combinations thereof. Hydrogenated versions of the above compounds, may also be used, for example, hydrogenated bisphenol A. Examples of halogenated versions of the above compounds include tetra-bromo bisphenol A and fluorenbisphenol, among others. An example of a nitrogen substituted version of the above compounds is (N,N)-diallyl-p-aminophenol.

Further ether compounds represented in this category include allyl ethers of novolac compounds. Examples of the phenol used for forming novolac resin include phenol, m-cresol, p-cresol, o-cresol, xylenols such as 2,3-xylenol, 2,5-xylenol, 3,5-xylenol and 3,4-xylenol; alkylphenols such as m-ethylphenol, p-ethylphenol, o-ethylphenol, 2,3,5-trimethylphenol, 2,3,5-triethylphenol, 4-tert-butylphenol, 3-tert-butylphenol, 2-tert-butylphenol, 2-tert-butyl-4-methylphenol and 2-tert-butyl-5-methylphenol; alkoxyphenols such as p-methoxyphenol, m-methoxyphenol, p-ethoxyphenol, m-ethoxyphenol, p-propoxyphenol, and m-propoxyphenol; isopropenylphenols such as o-isopropenylphenol, p-isopropenylphenol, 2-methyl-4-isopropenylphenol and 2-ethyl-4- isopropenylphenol; arylphenols such as phenylphenol; and polyhydroxyphenols such as 4,4'-dihydroxybiphenyl, bisphenol A, resorcinol, hydro-quinone and pyrogallol. These phenols may be used either singularly, or in combinations of two or more compounds. Of the above phenols, m-cresol, p-cresol, 2,5-xylenol, 3,5-xylenol and 2,3,5-trimethylxylenol are preferred.

Examples of such novalacs are poly allyl ethers of phenolic novolac, and derivatives thereof, such as poly allyl ethers of dicyclopentadienenovolac, poly allyl ethers of o-cresol novolac, poly allyl ethers of bisphenol A formaldehyde novolac and Poly allyl ethers of bisphenol F formaldehyde novolac Additionally, epoxide compounds may be formed from N-allylamine compounds having one or more allyl groups. Epoxidation (oxidation) of such compounds may lead to the formation of the n-glycid class of compounds. Non-limiting examples of N-allylamine compounds for use in the epoxidation reaction described herein include the following: (N,N)-di allyl ether of aniline:

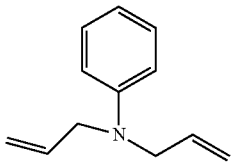

N,N,N',N'-tetra allyl a,a'-bis(4-amino-3,5 dimethylphenyl)p-diisopropylbenzene:

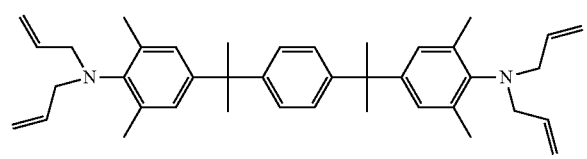 [SMILES: C=CCN(CC=C)c1c(C)cc(C(C)(C)c2ccc(C(C)(C)c3cc(C)c(N(CC=C)CC=C)c(C)c3)cc2)cc1C]

Tetra allyl methyleneaniline:

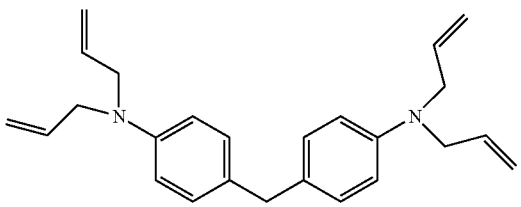 [SMILES: C=CCN(CC=C)c1ccc(Cc2ccc(N(CC=C)CC=C)cc2)cc1]

Alkylated MDA poly allyl/vinyl compound:

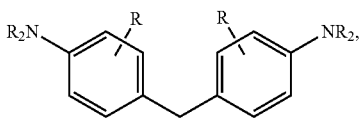

wherein each R is independently a hydrogen atom, a vinyl group, or an allyl group with at least one R being a vinyl group or an allyl group.

One or more of the above compounds allyl ethers, vinyl ethers, or N-allylamines may be used respectively as the allyl ether, vinyl ether, or N-allylamine in the process described herein. Additionally, one or more allyl ethers, vinyl ethers, or both may be used for the reaction. In one embodiment, an allyl ether and a vinyl ether may be present in the process reactions described herein in one molecule or in two or more molecules. Additionally, one or more of the respective allyl ethers and one or more of the vinyl ethers may respectively be used in the reaction as described above.

The catalytic oxidation may be performed in a batch process, in a continuous process or in a semi-continuous process. Indeed, the process may be modified in various aspects without departing from the gist of the invention.

The catalytic oxidation may be performed in a common stirred tank reactor provided with a means of stirring. The catalyst, aqueous reaction medium and reactants may be added in batch, or the reactants may be added over a period of time. If hydrogen peroxide is added during the reaction, then it is added to either the (stirred) organic phase comprising the reactant, if any, or the (stirred) aqueous reaction medium. In (semi)continuous operations, various recycling streams may be used to control the reaction conditions (maintained at a temperature of between −5° C. and 40° C.) and to optimize the production rate.

By way of general example the catalytic oxidations of allyl n-butyl ether and n-butyl vinyl ether are described hereafter. The following examples will more fully illustrate selected embodiments of this invention. All parts, percentages and proportions referred to herein and in the appended claims are by weight unless otherwise indicated.

EXPERIMENTAL

The catalytic oxidation may be carried out with a binuclear manganese complex as catalyst of the formula:

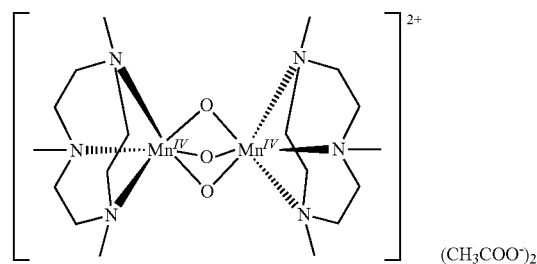

In the examples according to the invention an oxalate/oxalic acid buffer can be used, with 35% aqueous $H_2O_2$ as oxidant, and water (pure) as aqueous reaction medium. The experiments can be carried out with allyl n-butyl ether and n-butyl vinyl ether as starting materials. Examples 1 and 2 illustrate how the invention may be performed.

Example 1

Catalytic epoxidation of allyl n-butyl ether can be carried out with $[(TmTacn)_2 Mn^{IV}_2(\mu-O)_3]^{2+}(CH_3COO^-)_2$ as catalyst at 5° C. in a four necked glass reactor facilitated with a mechanical stirrer, cooling jacket and a bottom valve.

The ratio of catalyst: co-catalysts can be 1: 60. Thus, about 23 μmol of catalyst can be added in 100 mL of water followed by the addition of 0.675 mmol of sodium oxalate and 0.675 mmol of oxalic acid into the glass reactor under stirring conditions. The reaction can be initiated with the addition of dilute $H_2O_2$ as oxidant. Total 300 mmol of oxidant should be added, for instance with a flow rate of 10 mL/h into the reaction solution. Dosing of oxidant can be completed within the first 2.8 h and the reaction can be continued for a short period thereafter. After the reaction the aqueous solution in the reactor may be analyzed to determine the residual level of $H_2O_2$. The unreacted hydrogen peroxide in the reactor can be killed with $Na_2SO_3$. Then the aqueous and organic solution in the reactor can be analyzed by GC to determine the amount of epoxidation of the reaction.

Example 2

Catalytic epoxidation of the n-butyl vinyl ether of can be carried out similar to example 1. The reaction can be carried out with $[(TmTacn)_2 Mn^{IV}_2(\mu-O)_3]^{2+}(CH_3COO^-)_2$ as catalyst at 5° C. in a four necked glass reactor facilitated with a mechanical stirrer, cooling jacket and a bottom valve.

The reactivity and the product selectivity for ethyl vinyl ether is expected to be less than the corresponding ethyl allyl ether. This is due to the fact that C=C bond in the vinyl group is conjugated with the C—O bond making it electronically more deficient than the C=C in the allyl group. After the reaction the aqueous solution in the reactor may be analyzed to determine the residual level of $H_2O_2$. The unreacted hydrogen peroxide in the reactor can be killed with $Na_2SO_3$ Then the aqueous and organic solution in the reactor can be analyzed by GC.

The invention claimed is:

1. A process for the manufacture of an epoxyethyl ether or a glycidyl ether, comprising:
reacting a vinyl ether or an allyl ether with an oxidant in the presence of a water-soluble manganese complex in an aqueous reaction medium, wherein the water-soluble manganese complex comprises an oxidation catalyst, characterized in that the water-soluble manganese complex is a mononuclear complex of the formula (I):

[LMnX$_3$]Y  (I)

or a binuclear complex of the formula (II):

[LMn(μ-X)$_3$MnL](Y)$_n$  (II)

wherein Mn is a manganese; L or each L independently is a polydentate ligand, each X independently is a coordinating species and each μ-X independently is a bridging coordinating species, wherein Y is an anion, n is 1 or 2, and wherein the reaction is performed at a pH in the range of from 1.0 to 6.0 and the molar ratio of the vinyl ether or the allyl ether to the oxidant is from an excess vinyl ether or the allyl ether to 12:1, wherein each polydentate ligand is independently selected from acyclic compounds having at least 7 atoms in the backbone or cyclic compounds having at least 9 atoms in the ring, wherein each polydentate ligand having 3 nitrogen atoms with the nitrogen atoms separated by at least two carbon atoms, and wherein the oxidant comprises hydrogen peroxide, dilute hydrogen peroxide, or is selected from group consisting of organic peroxides, peracids, and combinations thereof.

2. The process of claim 1 wherein each X is independently a coordinating species and each μ-X is independently a bridging coordinating species, selected from the group consisting of: $RO^-$, $Cl^-$, $Br^-$, $I^-$, $F^-$, $NCS^-$, $N_3^-$, $I_3^-$, $NH_3$, $NR_3$, $RCOO^-$, $RSO_3^-$, $RSO_4^-$, $OH^-$, $O^{2-}$, $O_2^{2-}$, $HOO^-$, $H_2O$, $SH^-$, $CN^-$, $OCN^-$, and $S_4^{2-}$ and combinations thereof, wherein R is a $C_1$-$C_{20}$ radical selected from the group consisting of alkyl, cycloalkyl, aryl, benzyl and combinations thereof.

3. The process of claim 1, wherein each polydentate ligand is independently selected from triazacyclononane and 1,4,7-trimethyl-1,4,7,-triazacyclononane.

4. The process of claim 1, wherein a binuclear water-soluble manganese complex is used as an oxidation catalyst.

5. The process of claim 1, wherein the catalyst is used in a molar ratio of catalyst (Mn) versus the oxidant of from 1:10 to 1:10,000,000.

6. The process of claim 1, wherein the aqueous reaction medium is a water phase, comprising less than 10% by volume of co-solvents.

7. The process of claim 1, wherein the aqueous reaction medium further comprises an organic acid-salt combination buffer system.

8. The process of claim 1, wherein the reaction is carried out at temperatures in the range from −5° C. and 40° C.

9. The process of claim 1, wherein the oxidant comprises hydrogen peroxide and is an aqueous solution in a concentration of from 15% to 98%.

10. The process of claim 1, wherein the vinyl ether or the allyl ether is a mono alcohol, a diol, a triol a tetraol or a polyol molecule having one or more ether groups within the molecule.

11. The process of claim 10, wherein the vinyl ether or the allyl ether is an aliphatic or aromatic alcohol.

12. The process of claim 1, wherein the vinyl ether or the allyl ether having the formulae:

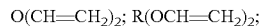

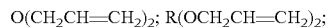

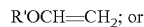

wherein R is a radical of 1 to 20 carbon atoms optionally having one or more heteroatoms and R' is a divalent radical of 1 to 20 carbon atoms.

13. The process of claim 1, wherein the vinyl ether or allyl ether is selected from ethers of aliphatic alcohols, polyglycols, fatty alcohols, carbohydrates, benzyl alcohols, phenol, phenol derivatives, novalac resins, and combinations thereof, wherein the phenol derivatives are selected from the group consisting of phenol, 4-tert-butylphenol, 2,4-dibromophenol, 4-(1,1,3,3)-tetramethylbutylphenol, 4-(2-phenylisopropyl) phenol, nonylphenol, o-cresol, p-methoxyphenol, bisphenol A, tetra-bromo bisphenol A, bisphenol S, bisphenol F, bisphenol P, bisphenol M, p-tert butyl phenol, resorcine, styrenated phenol, tetraphenyloethane, trisphenol, benzyl alcohol, and combinations thereof, hydrogenated versions thereof, and halogenated versions thereof.

14. The process of claim 12, wherein the vinyl ether or allyl ether is selected from the group consisting of divinyl ether, diallyl ether, allyl n-butyl ether, n-butyl vinyl ether, vinyl allyl ether, ethyl vinyl ether, ethylene divinyl diether, and combinations thereof.

15. The process of claim 1, wherein the hydrogen peroxide is added to the aqueous reaction medium at a rate about equal to the reaction rate of the catalytic oxidation.

16. The process of claim 1, wherein the molar ratio of the a vinyl ether or the allyl ether to the oxidant is from 2:1 to about 12:1.

17. A process for the manufacture of an N-glycid compound, comprising:
reacting a N-allylamine with an oxidant in the presence of a water-soluble manganese complex in an aqueous reaction medium, wherein the water-soluble manganese complex comprises an oxidation catalyst, characterized in that the water-soluble manganese complex is a mononuclear complex of the formula (I):

[LMnX₃]Y  (I)

or a binuclear complex of the formula (II):

[LMn(μ-X)₃MnL](Y)$_n$  (II)

wherein Mn is a manganese; L or each L independently is a polydentate ligand, each X independently is a coordinating species and each μ-X independently is a bridging coordinating species, n is 1 or 2, and wherein Y comprises an anion selected from the group consisting of RO⁻, Cl⁻, Br⁻, I⁻, F⁻, SO$_4^{2-}$, RCOO⁻, PF$_6^-$, tosylate, triflate (CF$_3$SO$_3^-$) and a combination thereof with R once again being a C$_1$ to C$_{20}$ radical selected from the group consisting of alkyl, cycloalkyl, aryl, benzyl and combination thereof, wherein the molar ratio of the N-allylamine to the oxidant is from 1:1 to 12:1.

18. The process of claim 1, wherein the anion is selected from the group consisting of RO⁻, Cl⁻, Br⁻, I⁻, F⁻, SO$_4^{2-}$, RCOO⁻, PF$_6^-$, tosylate, triflate (CF$_3$SO$_3^-$) and a combination thereof with R once again being a C$_1$ to C$_{20}$ radical selected from the group consisting of alkyl, cycloalkyl, aryl, benzyl and combination thereof.

19. The process of claim 1, wherein the aqueous reaction medium has a pH in the range of from 2.0 to 5.0.

* * * * *